(12) United States Patent
Schwartz

(10) Patent No.: US 10,463,257 B2
(45) Date of Patent: Nov. 5, 2019

(54) SYSTEM AND METHOD FOR IDENTIFYING PHYSICAL PROPERTIES OF FEET

(71) Applicant: AETREX WORLDWIDE, INC., Teaneck, NJ (US)

(72) Inventor: Laurence Schwartz, Teaneck, NJ (US)

(73) Assignee: AETREX WORLDWIDE, INC., Teaneck, NJ (US)

( * ) Notice: Subject to any disclaimer, the term of this patent is extended or adjusted under 35 U.S.C. 154(b) by 2 days.

(21) Appl. No.: 15/475,101

(22) Filed: Mar. 30, 2017

(65) Prior Publication Data

US 2017/0281008 A1 Oct. 5, 2017

Related U.S. Application Data

(60) Provisional application No. 62/315,503, filed on Mar. 30, 2016.

(51) Int. Cl.
*A61B 5/00* (2006.01)
*A61B 5/103* (2006.01)
(Continued)

(52) U.S. Cl.
CPC .......... *A61B 5/0077* (2013.01); *A61B 5/1036* (2013.01); *A61B 5/1074* (2013.01); *A61B 5/1077* (2013.01); *A61B 5/1079* (2013.01); *A61B 5/742* (2013.01); *G06T 7/0012* (2013.01); *G06T 7/11* (2017.01); *G06T 7/12* (2017.01); *G06T 7/155* (2017.01); *G06T 7/194* (2017.01); *G06T 7/44* (2017.01); *H04N 5/2256* (2013.01); *H04N 5/2257* (2013.01); *H04N 13/254* (2018.05); *G06T 2207/10024* (2013.01);
(Continued)

(58) Field of Classification Search
CPC ... A61B 5/0077; A61B 5/1036; A61B 5/1074; A61B 5/1077; A61B 5/1079; A61B 5/742; G06T 2207/10024; G06T 2207/10028; G06T 2207/10048; G06T 2207/30196; G06T 7/0012; G06T 7/11; G06T 7/12; G06T 7/155; G06T 7/194; G06T 7/44; H04N 13/254; H04N 5/2256; H04N 5/2257; H04N 5/247
USPC .......................................................... 348/38
See application file for complete search history.

(56) References Cited

U.S. PATENT DOCUMENTS

| | | | | |
|---|---|---|---|---|
| 5,128,880 A | * | 7/1992 | White ............... | A61B 5/1036 33/512 |
| 5,195,030 A | * | 3/1993 | White ............... | A43D 119/00 705/27.2 |

(Continued)

FOREIGN PATENT DOCUMENTS

WO 2008057056 A1 5/2008

OTHER PUBLICATIONS

International Search Report, dated Jun. 16, 2017, and Written Opinion issued in corresponding PCT Application No. PCT/US2017/025209.

*Primary Examiner* — Tracy Y. Li
(74) *Attorney, Agent, or Firm* — Saul Ewing Arnstein & Lehr LLP

(57) ABSTRACT

The present invention is a system and method for identifying certain physical properties of human feet. The system uses electronic and optical elements to perform before and after pronation test and before and after arch tests (meaning before and after use of an orthotic), and develop a 360 degree, three-dimensional view of the foot.

3 Claims, 23 Drawing Sheets

(51) Int. Cl.

| | | |
|---|---|---|
| H04N 13/254 | (2018.01) | |
| A61B 5/107 | (2006.01) | |
| H04N 5/225 | (2006.01) | |
| G06T 7/194 | (2017.01) | |
| G06T 7/00 | (2017.01) | |
| G06T 7/11 | (2017.01) | |
| G06T 7/12 | (2017.01) | |
| G06T 7/155 | (2017.01) | |
| G06T 7/44 | (2017.01) | |
| H04N 5/247 | (2006.01) | |

(52) U.S. Cl.
CPC ............ *G06T 2207/10028* (2013.01); *G06T 2207/10048* (2013.01); *G06T 2207/30196* (2013.01); *H04N 5/247* (2013.01)

(56) References Cited

U.S. PATENT DOCUMENTS

| | | | | |
|---|---|---|---|---|
| 5,206,804 | A * | 4/1993 | Thies | A43D 119/00 705/26.7 |
| 5,216,594 | A * | 6/1993 | White | A43D 1/025 705/28 |
| 5,237,520 | A * | 8/1993 | White | A43D 1/025 12/142 N |
| 5,339,252 | A * | 8/1994 | White | A43D 1/025 12/146 L |
| 6,205,230 | B1 * | 3/2001 | Sundman | A61B 5/0064 382/100 |
| 6,289,107 | B1 | 9/2001 | Borchers et al. | |
| 6,331,893 | B1 | 12/2001 | Williams et al. | |
| 7,493,230 | B2 | 2/2009 | Schwartz et al. | |
| 9,996,981 | B1 | 6/2018 | Tran et al. | |
| 10,043,068 | B1 * | 8/2018 | Hansen | G06K 9/00362 |
| 2005/0061332 | A1 | 3/2005 | Greenawalt et al. | |
| 2006/0034548 | A1 * | 2/2006 | Pishdadian | A43D 1/025 382/312 |
| 2007/0142955 | A1 * | 6/2007 | Lin | A43D 1/025 700/117 |
| 2007/0211355 | A1 | 9/2007 | Dalbo et al. | |
| 2009/0076772 | A1 * | 3/2009 | Hinshaw | A43B 7/1465 702/167 |
| 2009/0183388 | A1 | 7/2009 | Miller et al. | |
| 2009/0247909 | A1 * | 10/2009 | Mukumoto | A43B 7/28 600/592 |
| 2013/0053677 | A1 * | 2/2013 | Schoenfeld | A61B 5/1074 600/407 |
| 2013/0174445 | A1 * | 7/2013 | Hakkala | A43B 7/28 36/43 |
| 2016/0015298 | A1 * | 1/2016 | Danenberg | A61B 5/1079 600/476 |
| 2016/0081435 | A1 * | 3/2016 | Marks | A43D 1/027 382/154 |
| 2016/0249807 | A1 * | 9/2016 | Mougin | A61B 5/0064 600/407 |
| 2017/0272728 | A1 * | 9/2017 | Rafii | H04N 13/239 |

\* cited by examiner

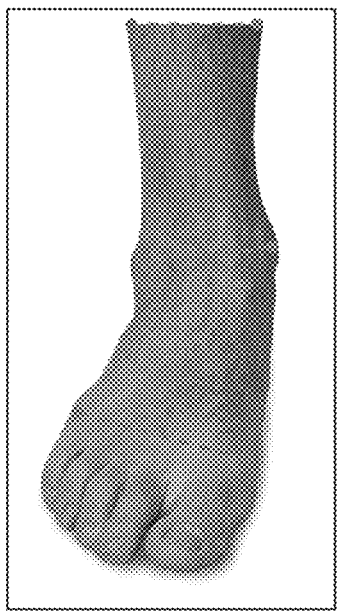
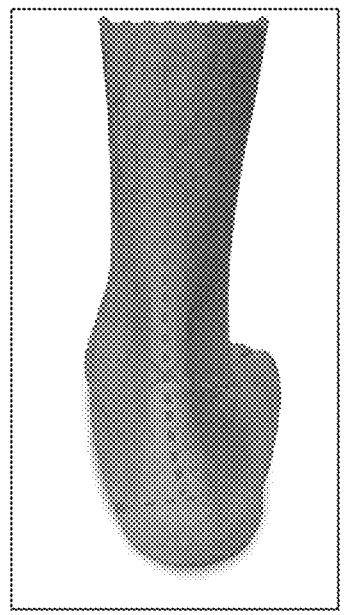
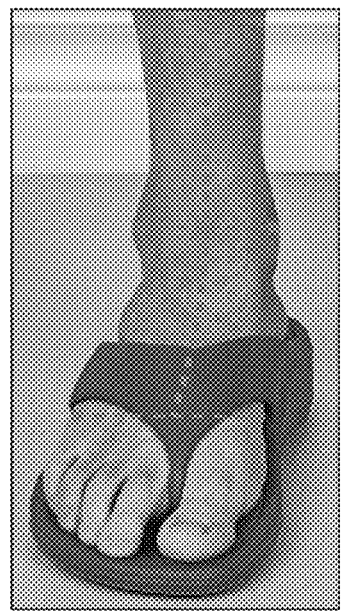
Figure 6A
Front
Figure 6B
Back
Figure 6C
Front with orthotic and/or footwear correction

SYSTEM AND METHOD FOR IDENTIFYING PHYSICAL PROPERTIES OF FEET

CROSS-REFERENCE TO RELATED APPLICATIONS

This application is based on, and claims priority to, U.S. provisional Application No. 62/315,503, filed Mar. 30, 2016, the entire contents of which being fully incorporated herein by reference.

SUMMARY OF THE INVENTION

The present invention is a system and method for identifying certain physical properties of human feet. Although in a preferred embodiment the invention is described in connection with identifying certain physical properties of human feet, it is understood that the principles of the present invention can be used to identify physical properties of any object where its general overall shape is known in advance.

The preferred embodiment of the present invention, sometimes referred to as the "Albert™ device" or "Albert™ scanner," is an improvement to the Aetrex Nova scanner. The Aetrex Nova scanner is a system that measures human feet for the purpose of determining shoe size and insole type. The Nova scanner uses a pressure plate on which the consumer stands so that pressure points on the feet can be determined, and arrays of IR LEDs that measure lengths and widths. With a combination of both, the arch depth of a consumer can be determined and an appropriate orthotic and shoe size can be recommended based on this determination. No cameras are used with the Nova scanner.

The Albert™ scanner adds multiple capabilities to the Nova scanner, including, without limitation, adding the ability to perform before and after pronation test and before and after arch tests (meaning before and after use of an orthotic), and develop a 360 degree, three-dimensional view of the foot. Both the Nova scanner and the Albert™ scanner perform all measurements by using electronic and optical means and do not include any motors or moving parts (other than, perhaps, internal mechanisms that may be part of individual cameras, lens systems of the cameras, and the like).

In a preferred embodiment, the Albert™ scanner includes at least 16 cameras in the perimeter of the scanner to capture the view of the foot and additional at least 2 cameras to capture the alignment of the foot and to determine if a pronation or supination exists. It is understood that the number of cameras can be increased or decreased and the system will still function, with a lesser or higher degree of resolution depending on whether there are lesser or greater number of cameras used.

Albert™ Hardware Structure

A preferred embodiment of the Albert™ scanner includes the following relevant components:

Sixteen (16) Cameras on the perimeter of the scanner, to capture images allowing a 3D measurement of feet; by way of example only, these cameras can comprise an ELP-USBFHD01M-L36 cameras manufactured by Ailipu Technology Co., Ltd. Of Guangdong, China.

Two (2) Cameras parallel to (in front of or in back of) the standing position of the person, capturing images of the front or back of the foot, for pronation measurement. The example shown in FIG. 2 shows only a single set of cameras positioned in this manner; however, it is understood that a second set of two additional cameras could be situated across from the first two to enable simultaneous capturing of both front and back images without requiring the user to switch orientation.

A minimum of sixteen (16) white light LEDs, one per camera, situated next to and aimed at the same aiming point as the aiming point of the cameras, to illuminate the scene and remove shadow (example shown in FIG. 3A); a preferred embodiment (see FIG. 3B) has 32 white LEDs, two per camera, one on each side of each camera, each aimed at the aiming point of its associated camera. By way of example only, Applicant has found that MX6AWT-A1-0000-000C51 Cree® XLamps® manufactured by Cree, Inc. of Durham, N.C., can be used for the white LED's. Light guides to guide (redirect) the light from the white LED's upward from the PC board and inward towards the center of the pressure measurement board can be fabricated using known techniques and processes.

Sixteen (16) Colored LEDs (3 colors)—for providing ambient light and to enhance the appearance of the scanner itself (primarily for marketing purposes). By way of example only, Applicant has found that OVSTRGBB1CR8 3-color LED's manufactured by OPTEK Technology Inc. of Carrollton, Tex. can be used.

Eighteen (18) Lenses with IR-CUT filter (one per camera) (ordered from the same manufacture as the cameras)—to prevent IR light from distorting the colors of the images.

All cameras are connected to a rounded PCB internally, which serves as a hub for all cameras and LEDs and connects to a processer (e.g., a PC) via a connection (e.g., a USB connection, WiFi, Bluetooth, IP connection, and the like).

BRIEF DESCRIPTION OF THE DRAWINGS

FIG. 6A shows a front pronation test; FIG. 6B shows a back pronation test, and FIG. 6C shows a front pronation test with orthotic and/or footwear correction;

DETAILED DESCRIPTION OF THE INVENTION

The Albert™ scanner is operated using software which runs on a PC (or any other computation/processing device or means), and will allow users to test their feet in multiple ways, e.g., via a "one-step test" or "two-step test" or "three-step test."

During the one step test (see FIG. 4), the user stands with both feet on the pressure board, and the Albert™ scanner detects the user standing on the boards and the test can start automatically. During the test process, multiple pressure maps of the user's feet are gathered, pronation images are taken via the front/back cameras, and two widths (left and right) and the length of the longest foot are measured. At the end of the test the user is presented with (a) recommended orthotics, (b) a foot pressure map for both feet, and (c) details about his/her feet (such as shoe size, arch type (low, medium, high), metatarsal pressure, pressure distribution by quadrants and area of each quadrant, and the like).

Figure 5:
FIG. 5 illustrates a two-step test process.
Figure 5:
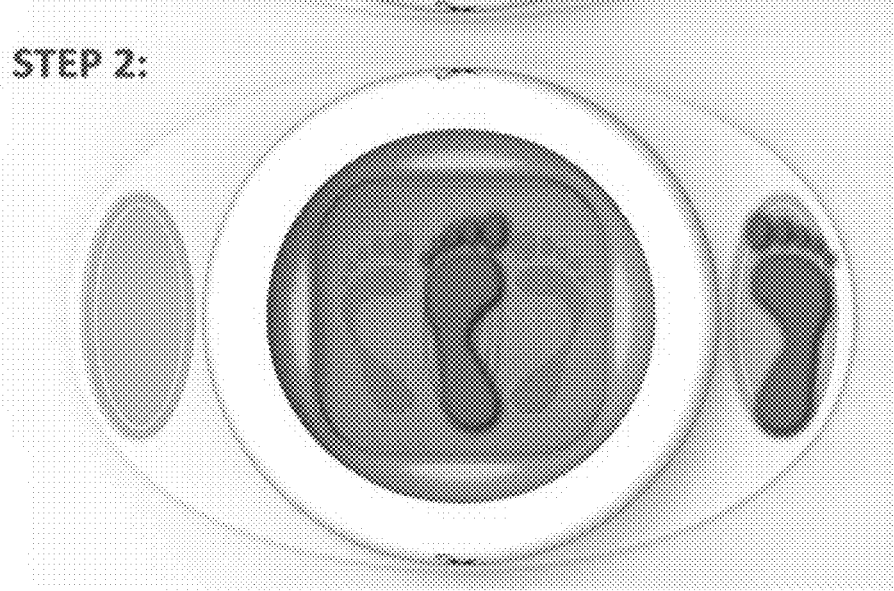
Figure 7:
FIG. 7 illustrates an Arch Test, where the red line shows the arch shape.
Figure 8:
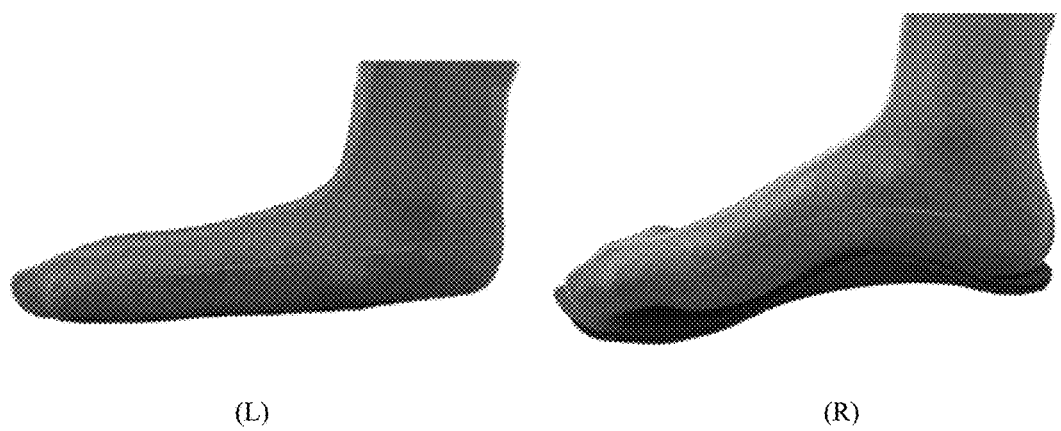
FIG. 8 illustrates an Arch Test, without orthotic (left) and with orthotic (right), where the red lines displays the arch's shape.

The two-step test is illustrated in FIG. 5. The order in which the feet are measured (right or left first) can be reversed, and the system can be configured to automatically detect which foot (right or left) is being measured. In the following example, the right foot is being measured first.

A three-step test is also possible and contemplated, which is the same as the two step test with an additional step that the foot pressure of both feet are measured simultaneously.

Figure 1:
FIG. 1 illustrates the Albert™ scanner.
Figure 2:
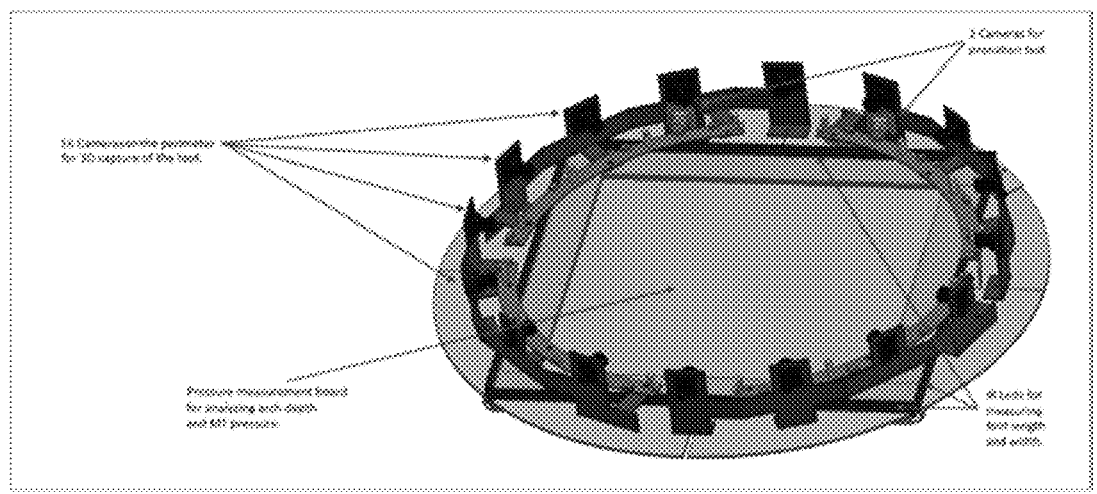
FIG. 2 illustrates examples of camera placement, on top of pressure plate and IR LED arrays.
Figure 3A:
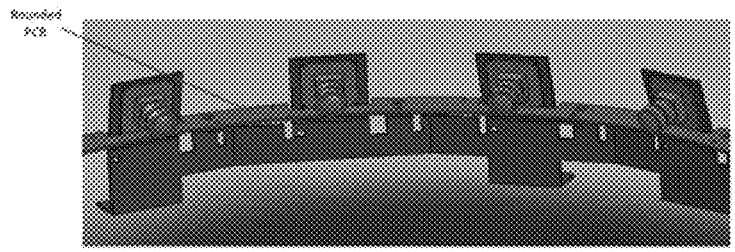
FIG. 3A illustrates a rounded PCB, where all LEDs and cameras are controlled by the PC individually.
Figure 3B:
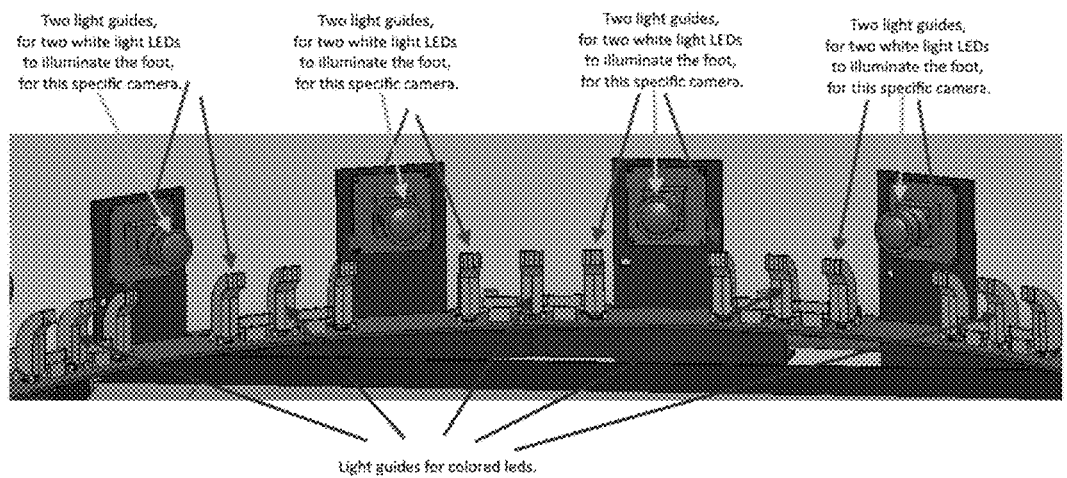
FIG. 3B illustrates a close-up of the configuration of FIG. 3A with 32 white LED's (two per camera) and a singled colored LED between each camera.
Figure 4:
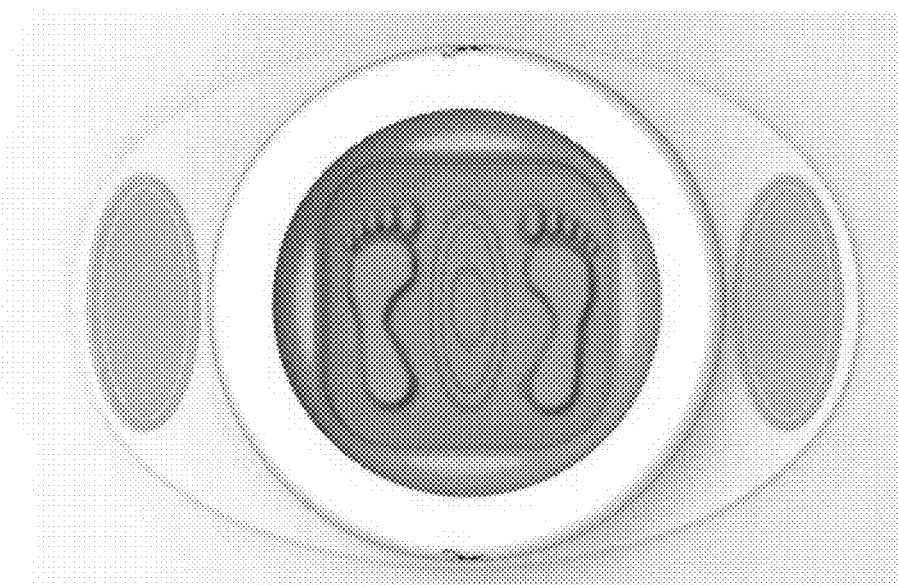
FIG. 4 illustrates a one-step test process.

During the first step, when the apparatus measures the right foot (in this example), the user stands with the right foot on the pressure plate and the left foot outside the measuring device on the foot bed designated area (e.g., the left grey oval shown in FIG. 4). During the second step, when the apparatus measures the left foot (in this example), the user stands with the left foot on the pressure plate and the right foot outside the measuring device on the foot bed designated area (the right grey oval shown in FIG. 4). During the test process (both first and second steps), multiple pressure maps of the user foot are gathered, pronation images are taken via the front/back cameras, each foot's width and length are measured, and 16 (in this example) images each of the user's feet are taken from 16 different angles. The data gathered from these measuring and imaging steps are processed via the processor(s) (e.g., the PC) and then the user is presented with recommended orthotics, a foot pressure map, details about his/her feet, and a 3D 360 degrees rotating view of his/her feet.

3D Test.

When the user feet are tested/measured, 16 images of each foot are taken from 16 different angles (surrounding the foot), and those images are used to create a 360 degree view of the feet, allowing the user to view his/her foot, rotate it and see it from all sides using an appropriate viewing system (e.g., software and/or hardware) developed for this purpose. To capture images of the foot of sufficient quality to perform a 3D reconstruction, an LED array is used to illuminate the foot from the same "viewing angle" as that of the camera and reduce the shadow created by the foot. For each camera, a lens is used that can capture the whole size of the foot, from any angle, with an IR-cut filter to prevent infrared light from distorting the colors of the image. In the next step, background images surrounding the foot are removed using a background removing algorithm, described below, to receive a clean image of the foot.

A key advantage of this test/measurement is to educate consumers about different aspects of their feet as their feet are measured and tested. Consumers are provided with a visual presentation of physical attributes of their feet and of how corrective measures such as the use of orthotics can improve alignment of their feet. The visual presentation includes 3D images showing pronation and other aspects of their feet.

Pronation Test.

When the user tests his/her feet, an image from the back (or front) of his/her feet is captured. As discussed above, in the "one-step test", images of both feet are taken simultaneously and in the "two-step test", images of first one foot and then the other are captured. Multiple key points are located at the outline of the foot by using a pronation detection algorithm and background removal algorithm (more on both in the algorithm section). By connecting the centers of those points an angled line is defined which shows visually (see FIGS. 6A and 6B) the alignment of the foot and if the foot is pronated or supinated.

One of the key advantages of the pronation test is that it allows a comparison of the angle of the pronation line of the persons foot, with orthotic and/or footwear correction and without. The user can visually see how the orthotic and/or footwear correction improves the alignment of his/her feet (see FIG. 6C).

Arch Shape Test.

The arch shape test identifies the shape of the arch of a person's foot from a side view (this is in addition to the arch depth test which is analyzed from the pressure board). This allows the user to view his/her arch condition and identify whether his/her arch collapsed (i.e. flat arch).

Arch Test—Before and after.

Another key advantage of the system is the "before and after arch shape test." After the first test is complete the user re-steps onto the pressure board, stepping on an orthotic, an additional side view image is taken. This test shows the user how his arch shape improves while wearing an orthotic. The orthotic type is recommended at the end of the initial test—which includes a few pressure points frames, length width and 16 pictures. At the end the user is presented with the test results: recommended orthotic, shoe size, arch depth etc. The Pronation test and Arch shape test are additional tests which are an option for the user to do after the initial test is completed. The one step test and two step test are only for the initial test.

Background Removal Algorithm Overview.

The applicant has developed algorithms to perform the above-described processes, both by using techniques known in the image processing and machine learning communities, and using filters developed by the Applicant. Some of the innovation lies in the use of dedicated filters suited for the apparatus, and in the use of methods originating from different theoretical communities (nonparametric statistics, machine learning).

It is well known that image segmentation (separation of foreground objects from the background in a given image) is a difficult task to automate, and a problem which is extremely difficult to solve perfectly on a large variety of images. To the best of Applicant's knowledge, methods which provide excellent success rates for the segmentation task rely on user-driven initializations or cumbersome statistical models and are time consuming (making them unsuited for real-time work), while faster methods usually provide results of lower quality, ranging from 40-70% success rate on real-life images.

The cornerstone of the proposed invention are algorithms for improving existing methods in the field which use all the known material elements of Applicant's new scanner, including:

(1) The background color of the system is light green, as uniform as possible, in order to create a strong contrast between a human foot (whether wearing a sock or not) and the background.

(2) The cameras installed on the scanner are static and therefore have, on the majority of the image, a static, known background (mostly of the scanner) and the rest is from the ambient environment of the "outside world" in which the scanner is located (mostly in the same areas). Therefore, relatively predictable images/pictures can be expected, without the motion noise or artifacts produced by moving cameras.

(3) In one embodiment, Applicant's system stores a series of background images, which are stored during a calibration phase. These background images are taken while no one is stepping on the scanner, and are thus merely plain background images. These background images are used during a test process as a comparison with the active (current) image, which contains a foot.

Figure 9:
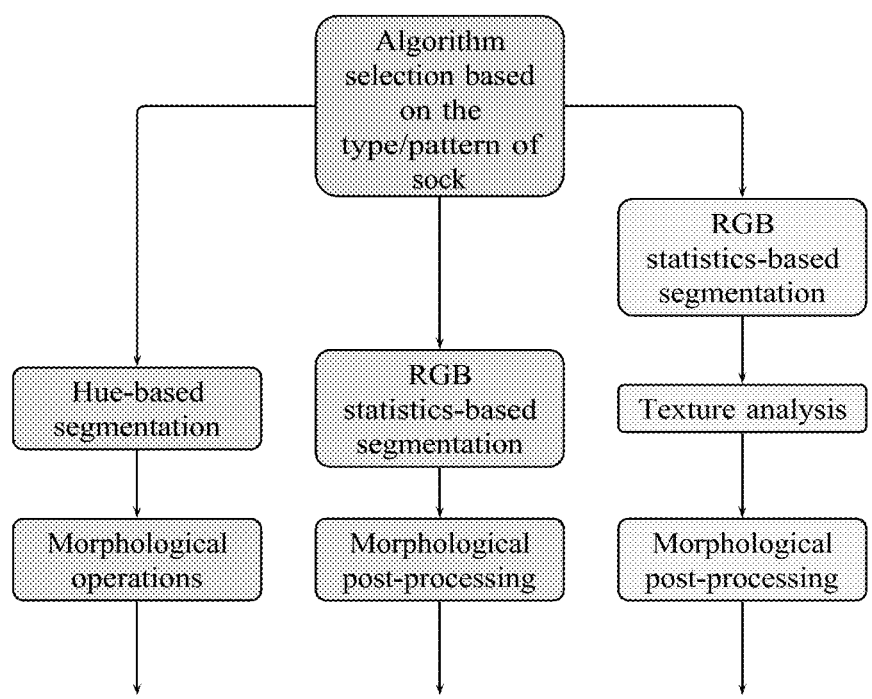
FIG. 9 is a flowchart illustrating the background removal algorithm.

The main algorithm is presented in FIG. 9. The first step of the background removal is running a small piece of code that determines what type of sock the person is wearing and based on that run the appropriate algorithm, which works best on removing the background around a specific sock. The three candidate algorithms are:

(1) An algorithm based on the analysis of the Hue, if the sock's color is very different from the light green's background.

(2) An algorithm based on a basic statistical analysis of the RGB components of the images, with and without foot.

(3) An algorithm based on the analysis of the image's texture, which aims to capture small, rapidly-changing variations in the image, which are most likely caused by the sock's cloth.

Hue-Based Segmentation.

Figure 10:
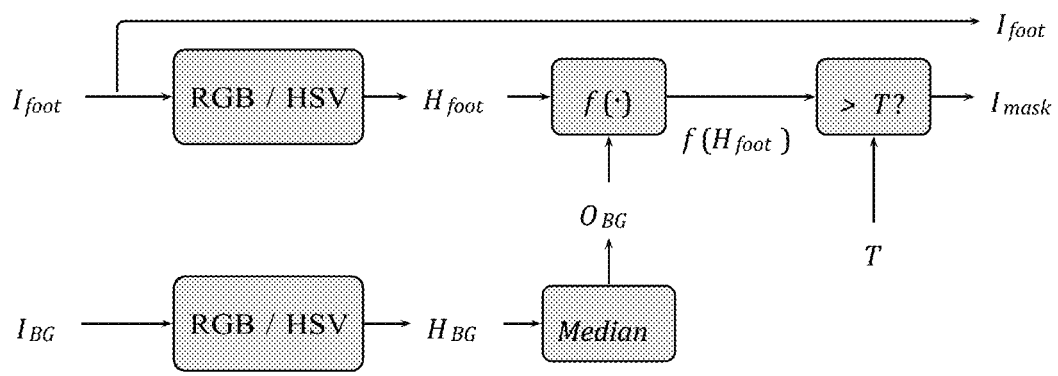
FIG. 10 illustrates the principle of the Hue-based background removal.

FIG. 10 presents an algorithm used for obtaining a preliminary mask based on the analysis of the hue.

The input to the Hue-based background removal algorithm comprises two pictures: one of the background only (which is taken offline, during a preliminary calibration procedure), denoted by $I_{BG}$, and one picture of the foot, $I_{foot}$, which also includes parts of the background that is desired to be removed. The first step of the algorithm is the extraction of the Hue of $I_{BG}$ and $I_{foot}$, respectively $H_{BG}$ and $H_{foot}$, using a regular conversion from RGB to HSV components. The hue of the background image, $H_{BG}$, is used to estimate the overall hue of the background, since the color of the background's apparatus is known and uniform. The estimate of the hue, $O_{BG}$, is computed as the median value of the hue values of each pixel. More precisely, the median of the pixels' hues can be found by arranging all the observations from lowest value to highest value and picking the middle one. If there is an even number of observations, then there is no single middle value; the median is then usually defined to be the mean of the two middle values, which corresponds to interpreting the median as the fully trimmed mid-range.

Given the estimate of the hue's background, $O_{BG}$, a nonlinear functional $f$ is applied on each pixel's hue of the foot image, $H_{BG}$. This step is performed in order to better separate the foot in its sock from the uniform background. In our numerical experiments, we chose $$f(x) = (x - O_{BG})^2,$$

though many other choices are of course possible. Given the resulting values $f(H_{foot})$, a thresholding operation is performed. Namely, we compare for each pixel the values $f(H_{foot})$ to a user-specified threshold T, and create a binary mask, denoted by $I_{mask}$; we obtain a binary image with the same dimensions of $I_{foot}$ and $I_{BG}$:

$$I_{mask} = \begin{cases} 1 & \text{if } f(H_{foot}) > T \\ 0 & \text{if } f(H_{foot}) \leq T \end{cases}$$

Figure 11:
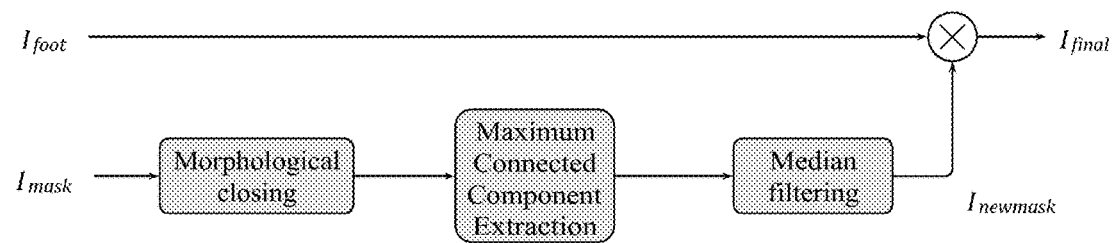
FIG. 11 illustrates the morphological operations performed after the hue-based method.

We then perform mathematical morphology operations in order to refine $I_{mask}$. Details of these operations are summarized in FIG. 11 (provided for purpose of example only), and their algorithmic description can be found in the literature. At first, we perform a morphological closing in order to suppress the small artifacts in $I_{mask}$, and to fill the holes in the zone containing the sock. After this step, the main blob in the resulting mask contains the sock; the next step therefore consists in extracting the biggest connected component in the mask. Eventually, a median filter is applied to smoothen the result, and make it more attractive to the eye.

The final image, $I_{final}$, is obtained by multiplying $I_{foot}$ by $I_{new\_mask}$ pixel by pixel. The resulting image includes the foot, and the background pixels are replaced by a black background.

RGB Statistics-Based Segmentation.

Figure 12:
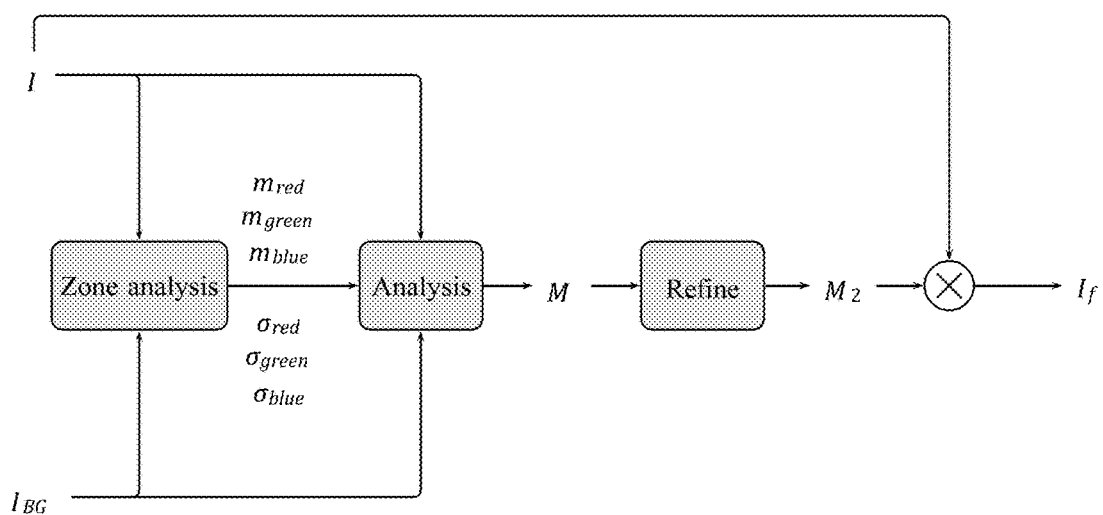
FIG. 12 is a block diagram of the background removal based on the RGB analysis.

The rationale of this background removal lies in the fact that we can identify the pixels belonging to the socks, based on a significant difference between their color and the background's color at the same position. The principle is summarized on FIG. 12.

We assume here that we have the same two pictures as in the Hue-based method above, one of the background $I_{BG}$ and one of the foot I. We also assume that the foot's location is approximately known, so that the lower part of the images $I_{BG}$ and I can be used to estimate the noise. The bottom of the image is denoted by A in the algorithm description, and includes N pixels; in practice, we consider the 100 last horizontal lines, since the foot lies in the upper part of the image. A preliminary segmentation can be performed as follows:

(1) We first compute the noise statistics from the difference between the two images (block "Zone Analysis" in FIG. 12):

$$[m_{red}, m_{green}, m_{blue}]^T = \frac{1}{N} \sum_{p \in A} (p_F - p_B)$$

$$[\sigma_{red}^2, \sigma_{green}^2, \sigma_{blue}^2]^T = \frac{1}{N}\sum_{p\in A}(p_F - p_B)^2 - \left(\frac{1}{N}\sum_{p\in A}(p_F - p_A)\right)^2,$$

where $p_F$ denotes pixel's RGB values in I, and $p_B$ denotes pixel's RGB values in $I_{BG}$.

(2) We perform an analysis of each pixel (block "Analysis" in FIG. 12) of I as follows: given a pixel F(i,j) with RGB components $(R_F, G_F, B_F)$ and its corresponding background pixel B(i,j) with RGB components $(R_B, G_B, B_B)$ if one of the following conditions $$m_{red} - 3\sigma_{red} \leq R_F - R_B \leq m_{red} + 3\sigma_{red}$$

$$m_{green} - 3\sigma_{green} \leq G_F - G_B \leq m_{green} + 3\sigma_{green}$$

$$m_{blue} - 3\sigma_{blue} \leq B_F - B_B \leq m_{blue} + 3\sigma_{blue}$$

holds, then the pixel is discarded as belonging to the background with a high probability, otherwise it is kept as possibly belonging to the foot, since we have a high discrepancy in at least one of the RGB components.

Figure 13:
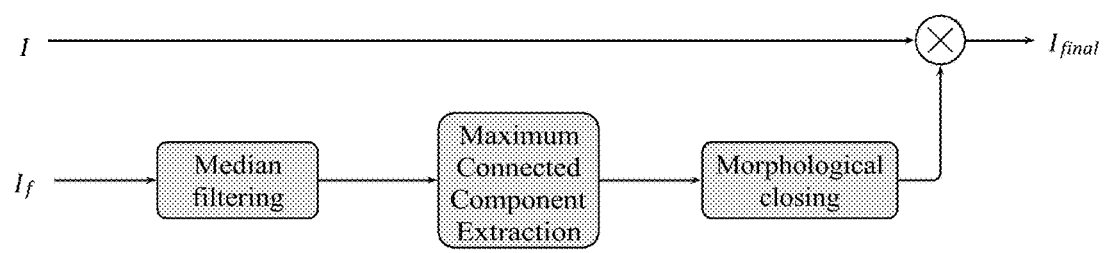
FIG. 13 illustrates the morphological operations performed after the RGB-based method.

(3) Mathematical morphology operations (block "Refine" in FIG. 12) are eventually performed to guarantee that a whole picture of the foot is saved. The details of the morphological operations are detailed in FIG. 13 (for purpose of example only): after a median filtering, the largest connected component is extracted. We apply to it a mathematical closing, and multiply the result by I to get the segmented image.

Texture Analysis.

If the sock contains patterns with the same color as the apparatus' background, the result mask after the RBG statistics-based segmentation needs to be improved. Following the type of sock, it might be necessary to provide a mask based on the analysis of the texture. The underlying idea is that the sock's texture contain more texture (small details and rapid changes) due to the type of cloth used in the sock, characterized by a rapidly-varying variance, whereas the background is smoother, and is characterized by a slowly-varying variance.

Figure 14:
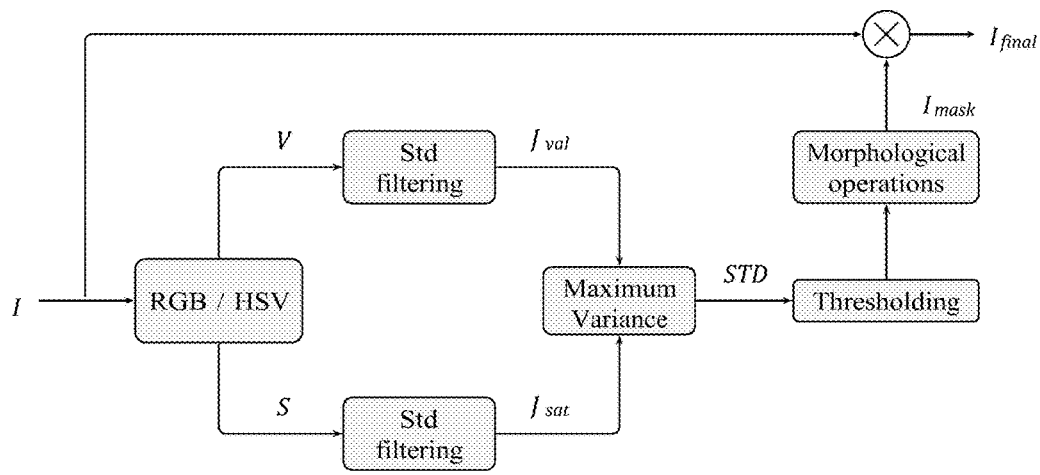
FIG. 14 is a block diagram illustrating texture analysis'

The details of the method are summarized in FIG. 14. The image containing the foot, I, is converted from RGB to HSV encoding. Since we want to analyze the texture, we focus this time on the value (V) and the saturation (S). We perform on each of these components a local standard deviation filtering; that is, we estimate for each pixel the local standard deviation on a square of 10×10 pixels: a low value refers to a background pixel, a high value refers more likely to a textured part (sock). The resulting pictures $J_{val}$ and $J_{sat}$ are then compared, and a new image STD is computed:

$$STD = \max\{J_{val}, J_{sat}\}.$$

Figure 15:
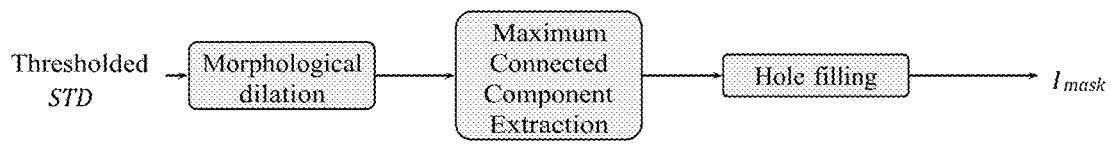
FIG. 15 illustrates the morphological operations performed after the texture-based method.

We perform on STD a threshold operation, in order to discard small artifacts from the results, which are more likely caused by additional noise on the image, and eventually morphological operations; a final binary mask $I_{mask}$ is provided, and is multiplied by the original image to perform the segmentation. The detail of the morphological operations is provided in FIG. 15.

Post-Processing Morphological Operations.

The segmented image obtained might need to be refined after the use of either algorithm aforementioned. Therefore, we perform a post-processing based on mathematical morphology standard operations [5]. The order of the operations differ accordingly to the algorithm used, but always include an geodesic dilation, taking the maximum connected component, morphological openings and closings and a final median filtering to smoothen the result.

Pronation Detection.

The detection of the pronation lies on the fact that we obtained a segmentation of the foot's image of sufficient quality, since representative points must be put on the contours of the feet. However, even with an excellent segmentation, finding the relevant points remains a difficult issue to address.

Figure 16:
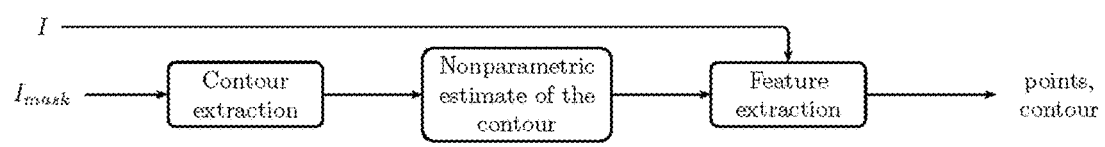
FIG. 16 illustrates the schematics for the pronation's detection.
Figure 17:
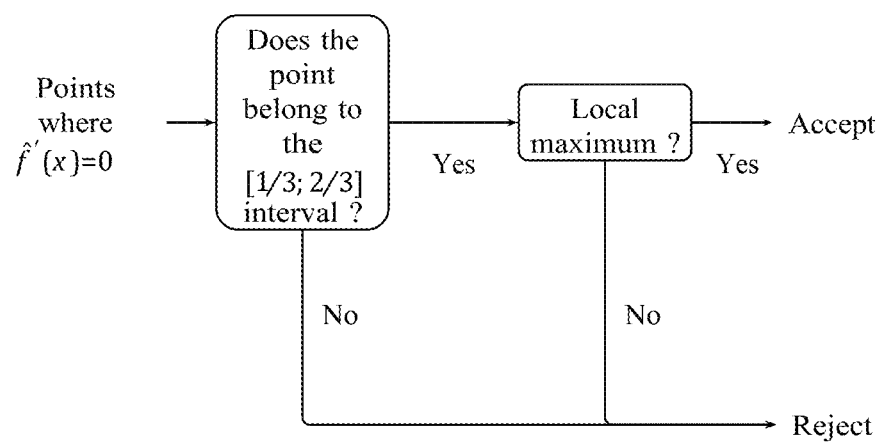
FIG. 17 illustrates middle points extraction.

FIG. 16 provides the basis of the used methodology for the pronation detection.

The contour extraction from the mask $I_{mask}$ can be easily done by computing the norm of the gradient $$g = \sqrt{\left(\frac{\partial I_{mask}}{\partial x}\right)^2 + \left(\frac{\partial I_{mask}}{\partial y}\right)^2},$$

and keeping the positive values as points of the contour. We then wish to extract from this contour, C, the position of the ankles in the picture. As it can be seen from FIG. 6, the ankles' points can be seen as local extrema of the contour; however, we cannot extract the local extrema in a straightforward manner from the contours, since the curves obtained by connecting all the contours' points altogether are extremely noisy. Therefore, each contour is estimated by a known and smoother nonparametric regressor, the Nadaraya-Watson estimate [6]:

$$\hat{f}(x) = \frac{\sum_{(x_i,y_i)\in C} K\left(\frac{x - x_i}{h}\right) y_i}{\sum_{(x_i,y_i)\in C} K\left(\frac{x - x_i}{h}\right)}, \quad (1)$$

where $(x_i, y_i)$ are the points of the contour C, K is the Gaussian curve $(K(x) = e^{-x^2/2}/\sqrt{2\pi})$ and h is a bandwidth parameter with is tuned accordingly to the image's resolution. The use of Equation (1) naturally smoothens the contours of the foot, thus allowing the search of the ankles' points among those where $\hat{f}'(x) = 0$. In practice, we split the foot's image in two halves (left and right), and perform (1) on each half.

Once the contours have been estimated, we perform feature extraction from the contour; more specifically, we wish to extract multiple points which will characterize the pronation of the user's foot. By way of example only, and not limitation: two upper points, two middle points and two lower points. Note that the definition of the lower differs whether the pronation test is performed on front or back pictures, whereas the definition of middle and upper points remains invariant with the view.

In the above-reference example herein, among these multiple points the two upper points are extracted in a straightforward manner, since they necessarily appear at the upper border of the picture. The two middle points represent the foot's ankles; there are chosen among the points where $\hat{f}'(x) = 0$: more specifically, we retain the points which lie on the second third (for purpose of example only) of the mask where $\hat{f}'(x) = 0$, and select for each half the point which provides in the same region the maximum value. Eventually, the lower points are selected as the one being at 95% of the x-coordinate of the mask (of course, other choices are possible).

Other embodiments are directed to different background-removal algorithms. For example, instead of using foot images and background images, seed generation can be accomplished with a foot image alone (no comparison background images are needed and the segmentation is based on color, for example. This requires one single foot images without the need for the background images. The presegmentation is based on color analysis, but instead of looking at the difference between a foot image and a background image, this alternative embodiment identifies and discards the green parts of the foot image, thereby leaving just the foot portion of the foot image remaining. The segmentation is based on learning a RGB background statistical model, and using it to solve an optimization problem. Furthermore, the seed of the optimization problem is computed using a saliency map, including a decomposition of the image into superpixels using the SLIC algorithm, from which we compute features based on the level of green, the uniqueness and variability of the superpixels. In simple terms, the green background is "sensed" and removed using the superpixel decomposition and its associated saliency map.

Figure 18:
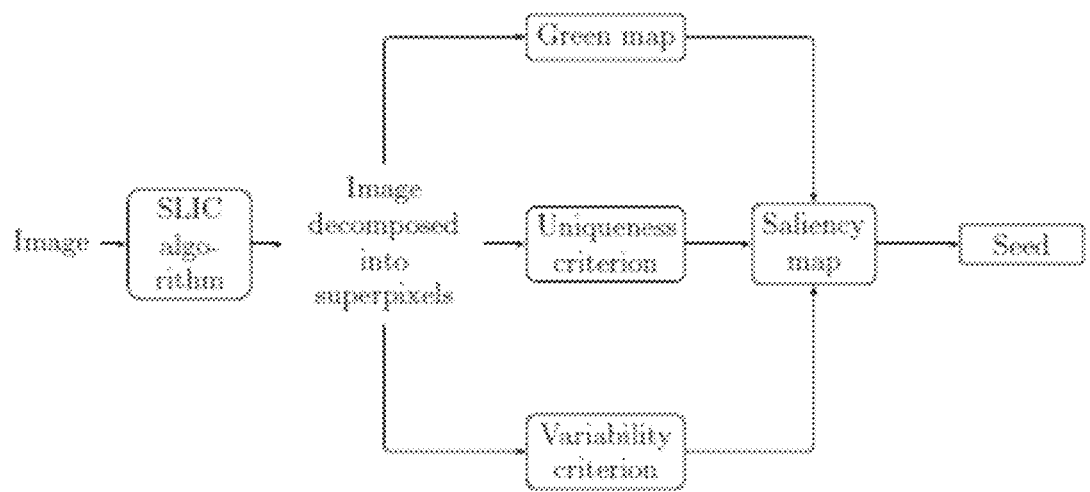
FIG. 18 illustrates an aspect of a second embodiment wherein superpixels which obtained the biggest scores are retained as the seed.

The presegmentation relies on known methods (see. e.g., Radhakrishna Achanta, Appu Shaji, Kevin Smith, Aurelien Lucchi, Pascal Fua (IEEE Transactions on Pattern Analysis and Machine Intelligence, vol. 34, num. 11, p. 2274-2282, May 2012), and Sabine Süsstrunk, SLIC Superpixels Compared to State-of-the-art Superpixel Methods and Federico Perazzi, Philipp Krähenbül, Yael Pritch, Alexander Hornung. Saliency Filters: Contrast Based Filtering for Salient Region Detection (IEEE CVPR, Providence, R.I., USA, Jun. 16-21, 2012). The image is first decomposed into superpixels. All superpixels are then sorted, using a green level evaluation method (this part is our contribution), a uniqueness and variability criterion, all of them are then combined to build a saliency map, which basically consists of attributing a score to each superpixel. Eventually, the superpixels which obtained the biggest scores are retained as the seed (see FIG. 18).

Figure 19:
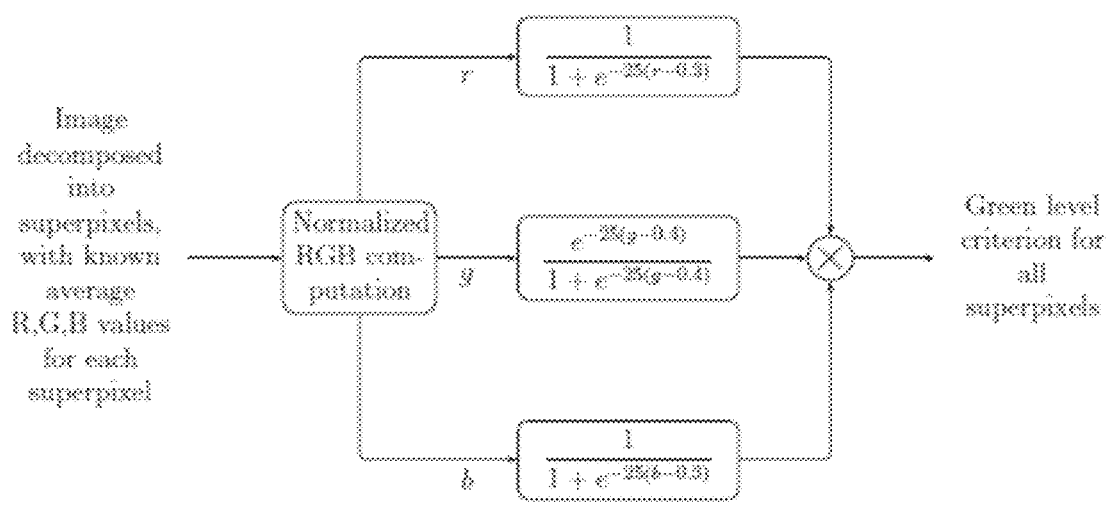
FIG. 19 illustrates the process of the color-based analysis according to a second embodiment.
Figure 20:
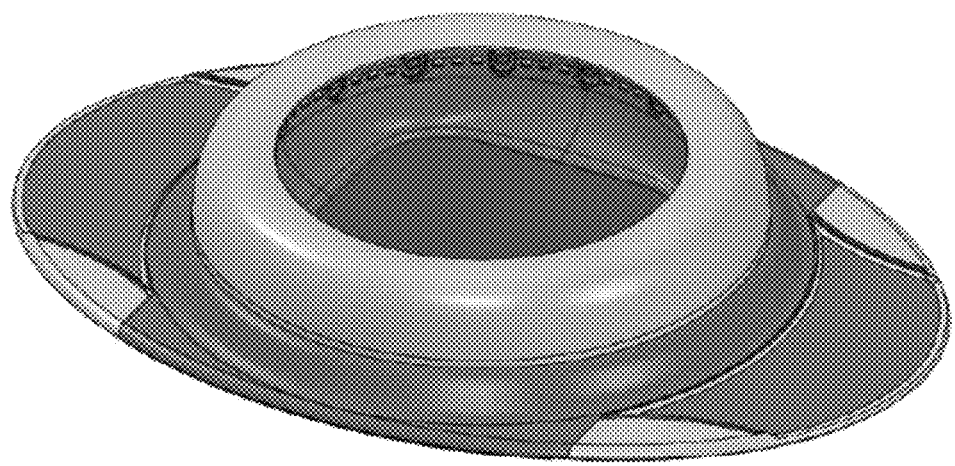
FIG. 20 is an alternative embodiment to the embodiment of FIG. 1.
Figure 21:
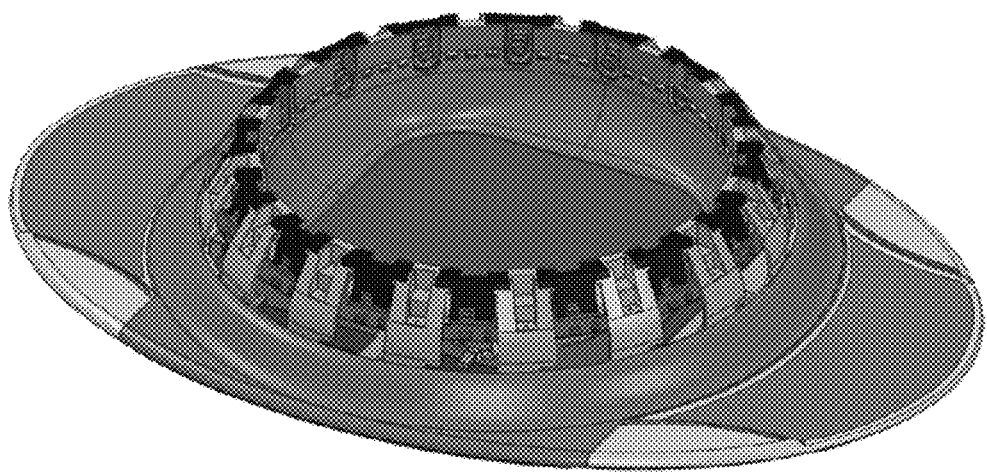
FIG. 21 is an alternative embodiment to the embodiment of FIG. 2.
Figure 22:
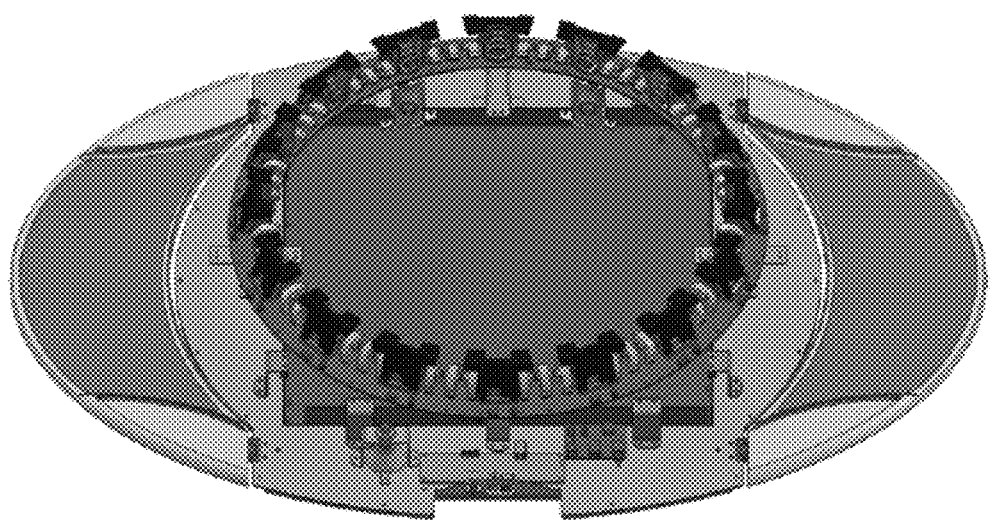
FIG. 22 is an alternative embodiment to the embodiment of FIG. 3A.
Figure 23:
FIG. 23 is an alternative embodiment to the embodiment of FIG. 3B.
Figure 24:
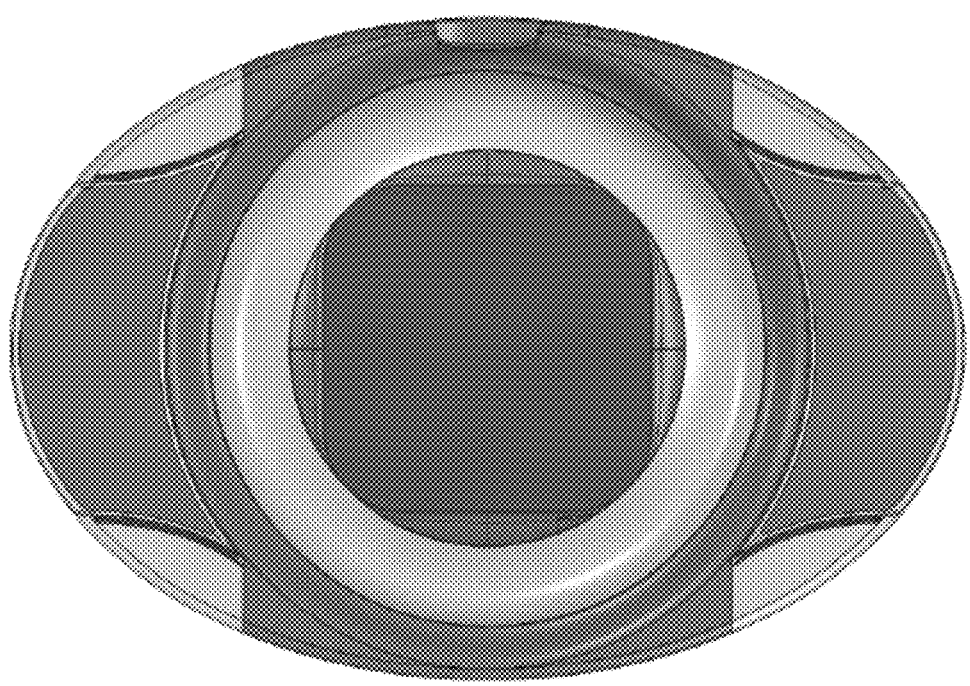
FIG. 24 is an alternative embodiment to the embodiment of FIG. 4.

The process of the color-based analysis according to this embodiment is illustrated in FIG. 19. The presegmentation is performed using a known algorithm, e.g., Superpixel, and the hue analysis for the segmentation can be preformed suing a known method, e.g., Grabcut ("GrabCut": interactive foreground extraction using iterated graph cuts, C. Rother, V. Kolmogorov, A. Blake, ACM SIGGRAPH 2004, pp 309-314).

Post-processing in this embodiment is performed using median filtering and additional standard operations. For example, first the segmented image is subjected to morphological operations (image closing, finding the biggest connected component), and then the image is resized to its original size. A median filtering is then performed to smoothen the result.

The second described embodiment uses methods that do not rely on any additional background image, and therefore the segmentation method is more reliable and less sensitive to lighting conditions. Moreover, they make more use of the statistical properties of the image, providing results with a higher level of confidence.

The above-described steps can be implemented using standard well-known programming techniques. The novelty of the above-described embodiment lies not in the specific programming techniques but in the use of the steps described to achieve the described results. Software programming code which embodies the present invention is typically stored in permanent storage. In a client/server environment, such software programming code may be stored with storage associated with a server. The software programming code may be embodied on any of a variety of known media for use with a data processing system, such as a diskette, or hard drive, or CD-ROM. The code may be distributed on such media, or may be distributed to users from the memory or storage of one computer system over a network of some type to other computer systems for use by users of such other systems. The techniques and methods for embodying software program code on physical media and/or distributing software code via networks are well known and will not be further discussed herein.

It will be understood that each element of the illustrations, and combinations of elements in the illustrations, can be implemented by general and/or special purpose hardware-based systems that perform the specified functions or steps, or by combinations of general and/or special-purpose hardware and computer instructions.

These program instructions may be provided to a processor to produce a machine, such that the instructions that execute on the processor create means for implementing the functions specified in the illustrations. The computer program instructions may be executed by a processor to cause a series of operational steps to be performed by the processor to produce a computer-implemented process such that the instructions that execute on the processor provide steps for implementing the functions specified in the illustrations. Accordingly, the figures support combinations of means for performing the specified functions, combinations of steps for performing the specified functions, and program instruction means for performing the specified functions.

While there has been described herein the principles of the invention, it is to be understood by those skilled in the art that this description is made only by way of example and not as a limitation to the scope of the invention. Accordingly, it is intended by the appended claims, to cover all modifications of the invention which fall within the true spirit and scope of the invention.

The functions of several elements may, in alternative embodiments, be carried out by fewer elements, or a single element. Similarly, in some embodiments, any functional element may perform fewer, or different, operations than those described with respect to the illustrated embodiment. Also, functional elements (e.g., modules, computers, and the like) shown as distinct for purposes of illustration can be incorporated within other functional elements, separated in different hardware, or distributed in a particular implementation.

While certain embodiments according to the invention have been described, the invention is not limited to just the described embodiments. Various changes and/or modifications can be made to any of the described embodiments without departing from the spirit or scope of the invention. Also, various combinations of elements, steps, features, and/or aspects of the described embodiments are possible and contemplated even if such combinations are not expressly identified herein.

INCORPORATION BY REFERENCE

The entire contents of all patents, published patent applications, provisional applications, and other references cited herein are hereby expressly incorporated herein in their entireties by reference.

The invention claimed is:

1. A system for identifying physical properties of human feet, comprising:

a processor configuring the system and receiving, analyzing, processing, and storing data related to physical properties of human feet;

a pressure-plate, coupled to the processor, measuring pressure points of the feet of persons when standing on the pressure plate;

an array of Infrared Light Emitting Diodes (IR LED's) coupled to the processor and configured by the processor to gather length and width measurements of the feet of persons when standing on the pressure plate;

a circular printed circuit board (PCB) coupled to the processor and situated around the pressure plate and providing a mounting perimeter around the pressure plate and encircling the feet of persons when standing on the pressure plate;

a plurality of cameras coupled to and situated in an approximately even distribution on the circular PCB, with lenses of the cameras aimed towards a center of the pressure plate;

whereby:

when a person stands on the pressure plate with a single foot, the processor operates the system to:

measure and store data related to pressure points and the length and width of the person's foot;

operate the plurality of cameras to capture and store a first set of images of the person's foot from each of the cameras; and process the stored data to produce for display a 360 degree, 3-dimensional image of the person's foot and information regarding the shoe size and insole type for the measured foot.

2. The system of claim 1, further comprising a set of front or back cameras having lenses positioned at the front or back of the system and directed towards a front or back foot position, respectively, of the person's foot, wherein when the person steps on the pressure plate, the processor operates the system to operate the front or back cameras to capture and store a second set of images of the person's foot from the front or back cameras and processes the front or back images to produce for display images showing pronation of the person's foot.

3. The system of claim 2, wherein after capturing, storing, and processing the second set of images, the processor operates the system to operate the front or back cameras to capture and store a third set of images of the person's foot, wearing an orthotic, and then processes the third set of front or back images to produce for display images showing pronation of the person's foot when wearing the orthotic.

* * * * *